(12) United States Patent
Lui et al.

(10) Patent No.: US 8,680,286 B2
(45) Date of Patent: Mar. 25, 2014

(54) METHOD FOR PRODUCING ENAMINOCARBONYL COMPOUNDS

(75) Inventors: Norbert Lui, Odenthal (DE); Jens-Dietmar Heinrich, Burscheid (DE)

(73) Assignee: Bayer Cropscience AG, Monheim (DE)

( * ) Notice: Subject to any disclaimer, the term of this patent is extended or adjusted under 35 U.S.C. 154(b) by 152 days.

(21) Appl. No.: 13/256,629

(22) PCT Filed: Mar. 12, 2010

(86) PCT No.: PCT/EP2010/001568
§ 371 (c)(1),
(2), (4) Date: Sep. 14, 2011

(87) PCT Pub. No.: WO2010/105772
PCT Pub. Date: Sep. 23, 2010

(65) Prior Publication Data
US 2012/0004416 A1    Jan. 5, 2012

(30) Foreign Application Priority Data
Mar. 16, 2009   (EP) .................................. 09155199

(51) Int. Cl.
*C07D 405/12*   (2006.01)

(52) U.S. Cl.
USPC ..................................................... 546/284.4

(58) Field of Classification Search
USPC ..................................................... 546/284.4
See application file for complete search history.

(56) References Cited

U.S. PATENT DOCUMENTS

| RE28,242 E | 11/1974 | Boosen et al. |
| 4,555,512 A | 11/1985 | Goldmann et al. |
| 2009/0247551 A1 | 10/2009 | Jeschke et al. |
| 2009/0253749 A1 | 10/2009 | Jeschke et al. |
| 2010/0190990 A1 | 7/2010 | Lui et al. |
| 2010/0240705 A1 | 9/2010 | Jeschke et al. |

FOREIGN PATENT DOCUMENTS

| CA | 1 225 094 | 8/1978 |
| CH | 503722 | 4/1971 |
| EP | 0123095 | 10/1984 |
| EP | 0153615 | 9/1985 |
| EP | 0 539 588 | 5/1993 |
| WO | 2007115643 | 10/2007 |
| WO | 2007115644 | 10/2007 |
| WO | 2007115646 | 10/2007 |
| WO | 2009/036899 | 3/2009 |

OTHER PUBLICATIONS

Dorwald, Side Reactions in Organic Synthesis, 2005, Wiley: VCH Weinheim Preface, pp. 1-15 & Chapter 8, pp. 279-308.*

International Search Report for PCT/EP2010/001568 Mailed Aug. 5, 2010.
European Search Report for EP09155199 Completed Jun. 4, 2009.
Greenhill et al., "A New and Easier Route to Tetronic Acid," Tetrahedron Letters No. 31, pp. 2686-2684, (1974).
Schmidt et al., "A Convenient Synthesis of 2,4(3H,5H)-Furandione (B-Tetronic Acid)1A." Synthetic Communications, vol. 11, No. 5, pp. 385-390, (1981).
Patai, "The Chemistry of Amino Group," Interscience Publishers, New York, pp. 45-52, (1986).
Shanadala et al., "Reaction of Methyl Tetronate With Some Amines, Synthesis of Substituted 4-Aminobut-2-Enolides," J. Heterocyclic Chem., vol. 21, pp. 1753-1754, (1984).
Wu et al., "Studies on Heterocyclic Compounds. VII. Syntheses of Novel Furo[2,3-B]Chromones [1]," J. Het. Chem., vol. 26, No. 3, pp. 605-608, (1989).
Mulholland et al., "A Synthesis of Tetronic Acid [Furan-2(3H,4(5H)-Dione] and Three Analogues." J. Chem. Soc. Perkin Trans. 1, vol. 1, No. 9-10, pp. 1225-1231, (1972).
Momose et al., "2(3H)- and 2(5H)-Furanones. III., An Efficient Synthesis and the Eschenmoser-Mannion Reaction of N-Substituted 4-Amino-2(5H)-Furanones," Heterocycles, vol. 27, No. 8, pp. 1907-1923, (1988).
Benary, "Ueber Die Einwirkung Von Chloracetylchlorid Auf Malonester Und Ueber Imido-Tetronaeure," Berichte der Deutchen chemischen Gesellschaft, vol. 45, pp. 3682-3686, (1912).
Stachel et al., "Die Synthese Van Piper Und Verwandten Tetronskuren," Tetrahedron Letters, vol. 21, No. 1, pp. 2891-2892, (1980).

\* cited by examiner

*Primary Examiner* — Patricia L Morris
(74) *Attorney, Agent, or Firm* — Miles & Stockbridge, P.C.

(57) ABSTRACT

The present invention relates to a process for preparing enaminocarbonyl compounds by reacting compounds of the formula (II)

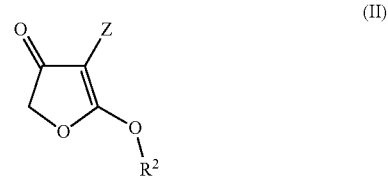

(II)

with compounds of the formula (III)

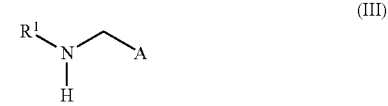

(III)

in which the A, $R^1$, $R^2$ and Z radicals are each as defined in the description, in the presence of a Brønsted acid.

9 Claims, No Drawings

METHOD FOR PRODUCING ENAMINOCARBONYL COMPOUNDS

CROSS REFERENCE TO RELATED APPLICATIONS

This application is a §371 National Stage Application of PCT/EP2010/001568, filed Mar. 12, 2010, which claims priority to European Application No. 09155199.4, filed Mar. 16, 2009.

BACKGROUND OF THE INVENTION

1. Field of the Invention

The present invention relates to a process for preparing enaminocarbonyl compounds.

2. Description of Related Art

Particular substituted enaminocarbonyl compounds are known as insecticidally active compounds from EP 0 539 588 A1. In addition, international patent applications WO 2007/115644, WO 2007/115643 and WO 2007/115646 also describe corresponding insecticidally active enaminocarbonyl compounds.

In general, enaminocarbonyl compounds are synthesized from tetronic acid and an amine according to scheme 1 below. This procedure is described, for example, in EP 0 539 588 A1 and in Heterocycles vol. 27, 8, pages 1907 to 1923 (1988).

Scheme 1:

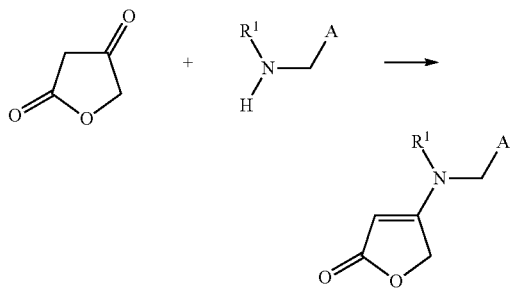

A particular disadvantage of this process is that anhydrous tetronic acid is required as a starting compound, the preparation of which is inconvenient and costly.

For instance, tetronic acid is generally prepared proceeding from ethyl acetoacetate via a bromination and subsequent hydrogenation (cf. Synthetic Communication, 11(5), pages 385 to 390 (1981)). The overall yield of tetronic acid proceeding from ethyl acetoacetate is less than 40%, which means that the process is not very attractive from an industrial point of view.

Swiss patent 503 722 describes a further process for preparing tetronic acid. This involves reacting ethyl 4-chloroacetoacetate with an aromatic amine to give 3-arylaminocrotonolactone, and then the tetronic acid is released by treatment with mineral acids. The disadvantage of this process is that the isolation of the tetronic acid is possible only by high-vacuum sublimation, which means that this process too is not very attractive from an industrial point of view.

A further process for preparing tetronic acid is described in EP 0 153 615 A, which proceeds from 2,4-dichloroacetoacetates. This likewise multistage and complicated process likewise affords the desired compound only with a moderate overall yield of 65%.

Tetrahedron Letters, 31, pages 2683 and 2684 (1974) describes the preparation of tetronic acid and of a corresponding enaminocarbonyl compound. The synthesis described there is reproduced in scheme 2 below. The reactant used is dimethyl acetylenedicarboxylate.

Scheme 2:

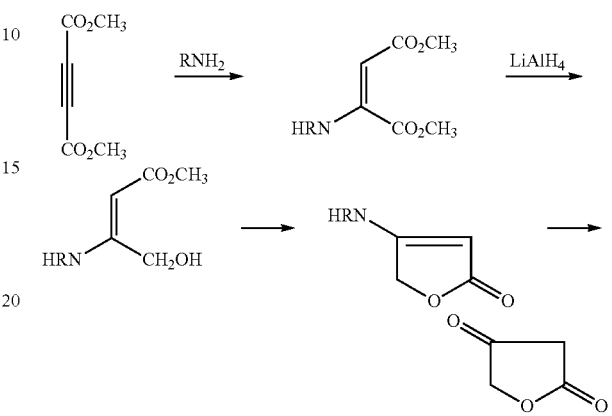

Disadvantages of this process are the low overall yield of only 30% and the requirement to use costly reactants, for example lithium aluminium hydride (LiAlH$_4$) as reagents.

Additionally known from the prior art is a process for preparing enaminocarbonyl compounds proceeding from methyl tetronate (J. Heterocyclic Chem., 21, 1753 (1984)). For this process, the starting material used is the costly 4-bromo-3-methoxybut-3-enecarboxylic ester.

A further process proceeds from a 4-chloroacetoacetic ester, which is reacted with amines (Heterocycles, vol. 27, 8, 1988, pages 1907 to 1923). The reaction to give the aminofuran is performed in one step. This involves adding the amine with glacial acetic acid to a solution of ethyl 4-chloroacetoacetate in benzene, and heating the resulting mixture under reflux for several hours. The yields of 4-methylamino-2(5H)-furanone in this synthesis are only 40%.

EP 0 123 095 A discloses a process in which tetronamide is prepared from 3-amino-4-acetoxycrotonic ester. 3-Amino-4-acetoxycrotonic ester is costly and inconvenient to prepare, and so an economically viable synthesis is not possible by this process.

A further process for preparing tetronic acid proceeding from malonic esters and chloroacetyl chloride is known from J. Chem. Soc., Perkin Trans. 1 (1972), 9/10, pages 1225 to 1231. This process affords the desired target compound with a yield of only 43%.

WO 2007/115644 describes the preparation of enaminocarbonyl compounds, for example of 4-[[(6-chloropyridin-3-yl)methyl](3,3-dichloroprop-2-en-1-yl)amino]furan-2(5H)-one by reaction of 4-[[(6-chloropyridin-3-yl)methyl]amino]furan-2(5H)-one with 3-bromo-1,1-dichloroprop-1-ene (cf. Preparation Example, Method 2, Example (3)). WO 2007/115644 also describes the preparation of enaminocarbonyl compounds, for example of 4-[[(6-chloropyridin-3-yl)methyl](2-fluoroethyl)amino]furan-2(5H)-one by reaction of 4-[[(2-fluoroethyl)amino]furan-2(5H)-one with 2-chloro-5-chloromethylpyridine (cf. Preparation Examples, Method 3, Example (4)). The reactions are preferably performed with hydrides of lithium or sodium. The substrates are generally costly and at the same time can be handled only with difficulty for safety reasons.

In WO 2009/036899, which claims the priority of European patent application 07116639, enaminocarbonyl compounds are prepared, for example, proceeding from 4-(methoxycarbonyl)-5-oxo-2,5-dihydrofuran-3-ol and an amine.

Scheme 3:

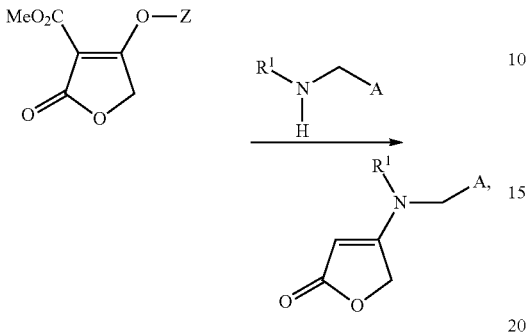

where

R$^1$ is hydrogen, alkyl, haloalkyl, alkenyl, haloalkenyl, alkynyl, cycloalkyl, cycloalkylalkyl, halocycloalkyl, alkoxy, alkyloxyalkyl, halocycloalkylalkyl or arylalkyl;

Z is hydrogen, alkali metal or alkaline earth metal; and

A is pyrid-2-yl or pyrid-4-yl, or is pyrid-3-yl which is optionally 6-substituted by fluorine, chlorine, bromine, methyl, trifluoromethyl or trifluoromethoxy, or is pyridazin-3-yl which is optionally 6-substituted by chlorine or methyl, or is pyrazin-3-yl or is 2-chloropyrazin-5-yl or is 1,3-thiazol-5-yl which is optionally 2-substituted by chlorine or methyl, or is pyrimidinyl, pyrazolyl, thiophenyl, oxazolyl, isoxazolyl, 1,2,4-oxadiazolyl, isothiazolyl, 1,2,4-triazolyl or 1,2,5-thiadiazolyl, which is optionally substituted by fluorine, chlorine, bromine, cyano, nitro, C$_1$-C$_4$-alkyl (which is optionally substituted by fluorine and/or chlorine), C$_1$-C$_3$-alkylthio (which is optionally substituted by fluorine and/or chlorine), or C$_1$-C$_3$-alkylsulphonyl (which is optionally substituted by fluorine and/or chlorine), or is

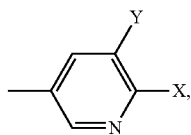

where

X is halogen, alkyl or haloalkyl and

Y is halogen, alkyl, haloalkyl, haloalkoxy, azido or cyano.

SUMMARY OF THE INVENTION

Proceeding from this prior art, it is an object of the present invention to provide an alternative process for preparing enaminocarbonyl compounds which is preferably simple and inexpensive to perform. The enaminocarbonyl compounds obtainable by this desired process should preferably be obtained with high yield and high purity. More particularly, the desired process should enable the desired target compounds to be obtained without the need for complex purification methods.

This object is achieved by a novel process for preparing enaminocarbonyl compounds of the general formula (I):

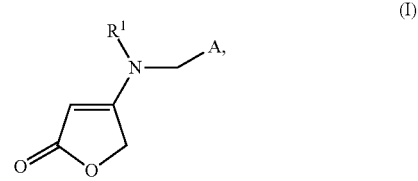

the process according to the invention being characterized in that compounds of the general formula (II)

are reacted with amines of the general formula (III)

where the individual radicals are defined as follows:

R$^1$ is hydrogen, alkyl, haloalkyl, alkenyl, haloalkenyl, alkynyl, cycloalkyl, cycloalkylalkyl, halocycloalkyl, alkoxy, alkyloxyalkyl, halocycloalkylalkyl or arylalkyl;

R$^2$ is alkyl, haloalkyl, alkenyl, haloalkenyl, alkynyl, cycloalkyl, cycloalkylalkyl, halocycloalkyl, alkyloxyalkyl, halocycloalkylalkyl, aryl or arylalkyl;

Z is selected from (C=O)OR$^3$ and (C=O)NR$^1$CH$_2$A, in which R$^3$ is selected from C$_{1-12}$-alkyl, C$_{3-8}$-cycloalkyl, C$_{2-12}$-alkenyl, C$_{2-12}$-alkynyl, C$_{6-8}$-aryl, C$_{7-19}$-arylalkyl or C$_{7-19}$-alkylaryl groups, each of which may be substituted by one or more groups selected from the group consisting of —R', —OR', —SR', —NR'$_2$, —SiR'$_3$, —COOR', —(C=O)R', —CN and —CONR$_2$', where R' is hydrogen or an C$_{1-12}$-alkyl group;

A is pyrid-2-yl or pyrid-4-yl, or is pyrid-3-yl which is optionally 6-substituted by fluorine, chlorine, bromine, methyl, trifluoromethyl or trifluoromethoxy, or is pyridazin-3-yl which is optionally 6-substituted by chlorine or methyl, or is pyrazin-3-yl or is 2-chloropyrazin-5-yl or is 1,3-thiazol-5-yl which is optionally 2-substituted by chlorine or methyl, or is pyrimidinyl, pyrazolyl, thiophenyl, oxazolyl, isoxazolyl, 1,2,4-oxadiazolyl, isothiazolyl, 1,2,4-triazolyl or 1,2,5-thiadiazolyl, which is optionally substituted by fluorine, chlorine, bromine, cyano, nitro, C$_1$-C$_4$-alkyl (which is optionally substituted by fluorine and/or chlorine), C$_1$-C$_3$-alkylthio (which is optionally substituted by fluorine and/or chlorine), or $C_1$-$C_3$-alkylsulphonyl (which is optionally substituted by fluorine and/or chlorine), or is

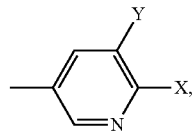

where
X is halogen, alkyl or haloalkyl and
Y is halogen, alkyl, haloalkyl, haloalkoxy, azido or cyano.

DETAILED DESCRIPTION OF A PREFERRED EMBODIMENT

It is thus envisaged in accordance with the invention that the desired enaminocarbonyl compounds of the formula (I) are prepared by a reaction of the corresponding compounds of the formula (II) with amines of the formula (III). The desired enaminocarbonyl compounds of the formula (I) are obtained with good yields in high purity under the reaction conditions specified in detail below, which means that the process according to the invention overcomes the disadvantages of the known processes. The desired compounds are obtained in a purity which generally does not necessitate an extensive workup of the direct reaction product.

Preferred, particularly preferred and very particularly preferred definitions of the A and $R^1$ radicals shown in the abovementioned general formulae (I) and (III) are given hereinafter.

A is preferably selected from the group consisting of 6-fluoropyrid-3-yl, 6-chloropyrid-3-yl, 6-bromopyrid-3-yl, 6-methylpyrid-3-yl, 6-trifluoromethylpyrid-3-yl, 6-trifluoromethoxy-pyrid-3-yl, 6-chloro-1,4-pyridazin-3-yl, 6-methyl-1,4-pyridazin-3-yl, 2-chloro-1,3-thiazol-5-yl or 2-methyl-1,3-thiazol-5-yl, 2-chloropyrimidin-5-yl, 2-trifluoromethylpyrimidin-5-yl, 5,6-difluoropyrid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrid-3-yl, 5-fluoro-6-bromopyrid-3-yl, 5-chloro-6-bromopyrid-3-yl, 5,6-dibromopyrid-3-yl, 5-fluoro-6-iodopyrid-3-yl, 5-chloro-6-iodopyrid-3-yl, 5-bromo-6-iodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl and 5-difluoromethyl-6-iodopyrid-3-yl.

$R^1$ is preferably selected from the group consisting of hydrogen, alkyl, haloalkyl, alkenyl, haloalkenyl, alkynyl, cycloalkyl, cycloalkylalkyl, halocycloalkyl, halocycloalkylalkyl and alkoxyalkyl.

A is more preferably selected from the group consisting of 6-fluoropyrid-3-yl, 6-chloropyrid-3-yl, 6-bromopyrid-3-yl, 6-chloro-1,4-pyridazin-3-yl, 2-chloro-1,3-thiazol-5-yl, 2-chloro-pyrimidin-5-yl, 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl, 5-chloro-6-iodopyrid-3-yl and 5-difluoromethyl-6-chloropyrid-3-yl.

$R^1$ is more preferably selected from the group consisting of methyl, ethyl, n-propyl, isopropyl, vinyl, allyl, propargyl, cyclopropyl, alkoxyalkyl, 2-fluoroethyl, 2,2-difluoroethyl and 2-fluorocyclopropyl.

A is most preferably selected from the group consisting of 6-chloropyrid-3-yl, 6-bromopyrid-3-yl, 6-chloro-1,4-pyridazin-3-yl, 2-chloro-1,3-thiazol-5-yl, 5-fluoro-6-chloropyrid-3-yl and 5-fluoro-6-bromopyrid-3-yl.

$R^1$ is most preferably selected from the group consisting of methyl, ethyl, n-propyl, isopropyl, n-prop-2-enyl, n-prop-2-ynyl, cyclopropyl, methoxyethyl, 2-fluoroethyl and 2,2-difluoroethyl.

Preferred, particularly preferred and very particularly preferred definitions of the Z and $R^2$ radicals shown in the abovementioned general formula (II) are given hereinafter.

Z is preferably selected from the group consisting of (C=O)$OR^3$, where $R^3$ is selected from $C_{1-12}$-alkyl, $C_{3-8}$-cycloalkyl, $C_{2-12}$-alkenyl, $C_{2-12}$-alkynyl, $C_{6-8}$-aryl, $C_{7-19}$-arylalkyl or $C_{7-19}$-alkylaryl groups, each of which may be substituted by one or more groups which are selected from the group consisting of —R', —OR', —SR', where R' is hydrogen or a $C_1$-$C_{12}$-alkyl group;

$R^2$ is preferably selected from the group consisting of alkyl, haloalkyl, alkenyl, haloalkenyl, cycloalkyl, alkyloxyalkyl or arylalkyl.

Z is more preferably selected from the group consisting of (C=O)$OR^3$ where $R^3$ is selected from methyl, ethyl, n-propyl, isopropyl or butyl;

$R^2$ is more preferably selected from the group consisting of $C_1$-$C_{12}$-alkyl.

Z is most preferably selected from the group consisting of (C=O)$OR^3$ where $R^3$ is selected from methyl and ethyl;

$R^2$ is most preferably selected from the group consisting of ethyl, isopropyl and butyl.

In a preferred embodiment, starting compounds of the formulae (II) and (III) are used in the process according to the invention, in which the substituents A, Z, $R^1$, $R^2$ and $R^3$ each have the abovementioned preferred definitions, it being possible to combine the preferred, particularly preferred and very preferred definitions of the substituents.

In a particularly preferred embodiment of the present invention, starting compounds of the general formulae (II) and (III) are used in the process according to the invention, in which the substituents A, Z, $R^1$, $R^2$ and $R^3$ each have the abovementioned particularly preferred definitions, it being possible to combine the preferred, particularly preferred and very preferred definitions of the substituents.

In a very particularly preferred embodiment of the present invention, starting compounds of the general formulae (II) and (III) are used in the process according to the invention, in which the substituents A, Z, $R^1$, $R^2$ and $R^3$ each have the abovementioned very particularly preferred definitions, it being possible to combine the preferred, particularly preferred and very preferred definitions of the substituents.

Unless mentioned otherwise, the term "alkyl", either in isolation or else in combination with further terms, for example haloalkyl, alkoxyalkyl, cycloalkylalkyl, halocycloalkylalkyl and arylalkyl, in the context of the present invention, is understood to mean a radical of a saturated aliphatic hydrocarbon group which has 1 to 12 carbon atoms and may be branched or unbranched. Examples of $C_1$-$C_{12}$-alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl, n-heptyl, n-octyl, n-nonyl, n-decyl, n-undecyl and n-dodecyl. Among these alkyl radicals, $C_1$-$C_6$-alkyl radicals are particularly preferred. Especially preferred are $C_1$-$C_4$-alkyl radicals, especially methyl and ethyl.

Unless mentioned otherwise, the term "alkenyl", either in isolation or else in combination with further terms, in accordance with the invention, is understood to mean a linear or branched $C_2$-$C_{12}$-alkenyl radical which has at least one double bond, for example vinyl, allyl, 1-propenyl, isopropenyl, 1-butenyl, 2-butenyl, 3-butenyl, 1,3-butadienyl, 1-pentenyl, 2-pentenyl, 3-pentenyl, 4-pentenyl, 1,3-pentadienyl, 1-hexenyl, 2-hexenyl, 3-hexenyl, 4-hexenyl, 5-hexenyl and 1,4-hexadienyl. Among these, preference is given to $C_2$-$C_6$-alkenyl radicals and particular preference to $C_2$-$C_4$-alkenyl radicals.

Unless mentioned otherwise, the term "alkynyl", either in isolation or else in combination with further terms, in accordance with the invention, is understood to mean a linear or branched $C_2$-$C_{12}$-alkynyl radical which has at least one triple bond, for example ethynyl, 1-propynyl and propargyl. Among these, preference is given to $C_3$-$C_6$-alkynyl radicals and particular preference to $C_3$-$C_4$-alkynyl radicals. The alkynyl radical may also have at least one double bond.

Unless mentioned otherwise, the term "cycloalkyl", either in isolation or else in combination with further terms, in accordance with the invention, is understood to mean a $C_3$-$C_8$-cycloalkyl radical, for example cyclopropyl, cyclobutyl, cyclopentyl, cyclohexyl, cycloheptyl and cyclooctyl. Among these, preference is given to $C_3$-$C_6$-cycloalkyl radicals.

Unless mentioned otherwise, the term "aryl" is understood in accordance with the invention to mean an aromatic radical having 6 to 14 carbon atoms, preferably phenyl.

Unless mentioned otherwise, the term "arylalkyl" is understood to mean a combination of "aryl" and "alkyl" radicals defined in accordance with the invention, the radical generally being bonded via the alkyl group. Examples thereof are benzyl, phenylethyl or α-methylbenzyl, particular preference being given to benzyl.

Unless mentioned otherwise, the term "halogen-substituted radicals" is understood to mean, for example, haloalkyl, radicals mono- or polyhalogenated up to the maximum possible number of substituents. In the case of polyhalogenation, the halogen atoms may be the same or different. Halogen is fluorine, chlorine, bromine or iodine, especially fluorine, chlorine or bromine.

Unless mentioned otherwise, the term "alkoxy", either in isolation or else in combination with further terms, for example haloalkoxy, in the present context is understood to mean an o-alkyl radical, where the term "alkyl" is as defined above.

Optionally substituted radicals may be mono- or polysubstituted, where the substituents may be the same or different in the case of polysubstitution.

Some of the compounds of the general formula (II) are known from the prior art (R. Anschültz, Chemische Berichte, 1912, 45, 2374; E. Benary, Chemische Berichte, 1912, 45, 3682; Kuo, Sheng Chut et al., Journal of Heterocyclic Chemistry, 1989, 26(3), 605-8) or can be prepared analogously.

The present invention further provides compounds of the formula (II)

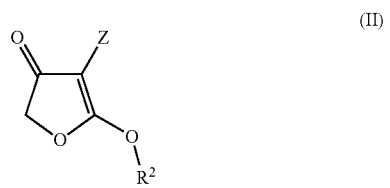

(II)

in which the Z and $R^2$ radicals are each as defined above, with the proviso that $R^2$ is not ethyl or phenyl.

The invention also provides a process for synthesizing correspondingly modified derivatives of the compounds of the general formula (II) according to scheme 4 below, for example proceeding from malonic acid derivatives of the general formula (IV) using chloroacetyl chloride in the presence of a base:

Scheme 4:

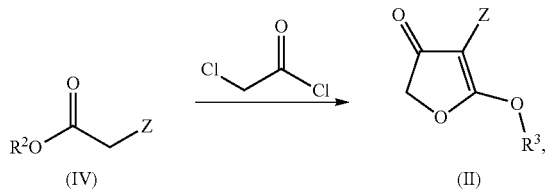

where Z and $R^2$ are each as defined above.

The malonic esters of the general formula (IV) used as reactants are commercially available or can be prepared by processes known from the prior art.

The amines of the general formula (III) required for the inventive reaction are commercially available or can be prepared by literature methods (cf., for example, S. Patai "The Chemistry of Amino Group", Interscience Publishers, New York, 1968).

The reaction of the compounds of the formula (II) with the amines of the formula (III) can be performed in the presence of solvents (diluents). Solvents are advantageously used in such an amount that the reaction mixture remains efficiently stirrable over the entire process. Useful solvents for performing the process according to the invention include all organic solvents which are inert under the reaction conditions.

Examples include: halohydrocarbons, especially chlorohydrocarbons, such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene; ethers such as ethyl propyl ether, methyl tert-butyl ether, n-butyl ether, anisole, phenetol, cyclohexyl methyl ether, dimethyl ether, diethyl ether, dimethylglycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, methyl-tetrahydrofuran, dioxane, dichlorodiethyl ether; methyl-THF and polyethers of ethylene oxide and/or propylene oxide; nitrohydrocarbons such as nitromethane, nitroethane, nitropropane, nitrobenzene, chloronitrobenzene, o-nitrotoluene; nitriles such as acetonitrile, methyl nitrile, propionitrile, butyronitrile, isobutyronitrile, benzonitrile, phenyl nitrile, m-chlorobenzonitrile, and compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide, diisoamyl sulphoxide; sulphones such as dimethyl, diethyl, dipropyl, dibutyl, diphenyl, dihexyl, methyl ethyl, ethyl propyl, ethyl isobutyl and pentamethylene sulphone; aliphatic, cycloaliphatic or aromatic hydrocarbons such as pentane, n-hexane, n-heptane, n-octane, nonane, for example what are known as white spirits with components with boiling points in the range, for example, from 40° C. to 250° C., Cymene, petroleum fractions within a boiling range from 70° C. to 190° C., cyclohexane, methylcyclohexane, petroleum ether, ligroin, octane, benzene, toluene, xylene; esters such as methyl, ethyl, butyl and isobutyl acetate, and dimethyl, dibutyl and ethylene carbonate; amides such as hexamethylenephosphoramide, formamide, N,N-dimethylacetamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-1,4-diformylpiperazine; and aliphatic alcohols such as methanol, ethanol, n-propanol and isopropanol and n-butanol.

The inventive reaction is preferably performed in a solvent which is selected from the group consisting of dioxane, butyronitrile, propionitrile, acetonitrile, DME, toluene, methyl-THF, dichlorobenzene, chlorobenzene, n-heptane, isobutanol, n-butanol, ethanol, methyl tert-butyl ether, isopropyl ethyl ether and mixtures thereof.

Optionally, it is also possible depending on the starting compounds to perform the reaction in substance, i.e. without addition of solvents.

The reaction can also be performed in the presence of water.

The reaction of the compounds of the formula (II) with the amines of the formula (III) is preferably performed in the presence of a Brønsted acid.

The molar ratio of the Brønsted acid and the amines of the formula (III) may vary. The ratio of the Brønsted acid to the amine of formula (III) preferably lies in the range of approximately 10:0.6 to approximately 1:1.5, particularly in the range of approximately 5:0.9 to 1:1.2, more particularly in the range of approximately 2:1 to approximately 1:1.1.

It is possible to use either organic or inorganic Brønsted acids. Preference is given to using inorganic acids, for example phosphoric acid ($H_3PO_4$), sulphuric acid ($H_2SO_4$), hydrochloric acid (HCl), hydrobromic acid (HBr), hydrofluoric acid (HF) or potassium hydrogensulphate ($KHSO_4$). The individual acids can be used either in anhydrous form or in hydrous form, for example as 85% phosphoric acid or 37% hydrochloric acid, i.e. more particularly in forms in which the acids are commercially available. Examples of suitable organic acids are trifluoroacetic acid, acetic acid, methanesulphonic acid and p-toluenesulphonic acid. Among the aforementioned acids, phosphoric acid, sulphuric acid, potassium hydrogensulphate and trifluoroacetic acid are especially preferred.

The reaction to prepare the compounds of the formula (I) can generally be performed under reduced pressure, at standard pressure or under elevated pressure. The temperatures employed may likewise vary depending on the substrates used, and are easy to determine by routine tests by the person skilled in the art. For example, the reaction to prepare the compounds of the formula (I) can be performed at a temperature of 20 to 200° C., preferably 20 to 150° C.

The stoichiometry of the starting compounds of the formulae (II) and (III) used may vary within wide ranges and is generally not subject to any particular restriction. Suitable stoichiometries of the starting compounds of the formulae (II) and (III) used can be determined easily by routine tests by the person skilled in the art. For instance, the molar ratio of the compound of the general formula (II) to the amine of the general formula (III) used may, for example, be 0.5 to 10, particularly 1to 6, especially 1.05 to 2. The use of greater amounts of compound of the formula (III) is possible in principle, but disadvantageous for economic reasons.

At the end of the reaction, the water of reaction can be removed as an azeotrope by distilling part of the solvent. In the case of high-boiling solvents, this can be done under reduced pressure. By virtue of this operation, a quantitative conversion is generally achieved.

If the reaction is performed in a solvent, the solvent can be removed by distillation after the end of the reaction. This can be done under standard pressure or reduced pressure, at room temperature or elevated temperatures.

The desired compounds of the formula (I) can also be isolated, for example, by crystallization.

The present invention is illustrated in detail by the examples which follow, though the examples should not be interpreted in such a manner as to restrict the invention.

PREPARATION EXAMPLES

Example 1

Preparation of 4-[[(6-chloropyridin-3-yl)methyl](2,2-difluoroethyl)amino]furan-2(5H)-one 31.2 g of potassium hydrogensulphate are added at room temperature to a suspension of 46 g of ethyl 2-ethoxy-4,5-dihydro-4-oxofuran-3-carboxylate and 39.3 g of N-[(6-chloropyridin-3-yl)methyl]-2,2-difluoroethylamine in 705 ml of butyronitrile. The mixture was heated to reflux for 5 hours. Subsequently, it was cooled to room temperature and washed with 890 ml of water. The solvent was removed under reduced pressure. This gave 51 g of 4-[[(6-chloropyridin-3-yl)methyl](2,2-difluoroethyl)amino]furan-2(5H)-one (this corresponds to a 93% yield).

$^1$H NMR ($CDCl_3$, 298K) δ: 3.53 (td, 2H), 4.52 (s, 2H), 4.82 (s, 2H), 4.83 (s, 1H), 5.96 (tt, 1H), 7.37 (d, 1H), 7.55 (dd, 1H), 8.27 (d, 1H)

Example 2

Preparation of isopropyl 2-isopropoxy-4,5-dihydro-4-oxofuran-3-carboxylate 20 g of diisopropyl malonate were initially charged in 173 g of toluene. Subsequently, 12 g of potassium tert-butoxide were added in portions at room temperature. After 2 hours, the solvent was removed under reduced pressure and admixed again with 173 g of toluene. At 0° C., 6 g of chloroacetyl chloride were added dropwise and the reaction mixture was then stirred at room temperature. Subsequently, 50 g of ice and 100 ml of water were added and the mixture was stirred for 10 minutes. The organic phase was removed and dried over magnesium sulphate. After the solvent had been removed, a 1:1 mixture of isopropyl 2-isopropoxy-4,5-dihydro-4-oxofuran-3-carboxylate (45% yield) and diisopropyl malonate was obtained. The mixture could be used thus in the next stage. With the aid of column chromatography, the isopropyl 2-isopropoxy-4,5-dihydro-4-oxofuran-3-carboxylate was isolated.

$^1$H NMR ($CDCl_3$, 298K) δ: 1.3 d (6H), 1.50 d (6H), 4.63 s (2H), 5.14 m (1H), 5.29 m (1H), 8.56 s (1H), 8.75 d(1H)

Example 3

Preparation of 4-[[(6-chloropyridin-3-yl)methyl](2,2-difluoroethyl)amino]furan-2(5H)-one 0.6 g of potassium hydrogensulphate was added at room temperature to a suspension of 1.0 g of isopropyl 2-isopropoxy-4,5-dihydro-4-oxofuran-3-carboxylate and 0.85 g of N-[(6-chloropyridin-3-yl)methyl]-2,2-difluoroethylamine in 15.8 g of butyronitrile. The mixture was heated to reflux for 5 hours. Subsequently, it was cooled to room temperature and washed with 10 ml of water. The solvent was removed under reduced pressure. This gave 1 g of 4-[[(6-chloropyridin-3-yl)methyl](2,2-difluoroethyl)amino]furan-2(5H)-one (this corresponds to 95% yield).

$^1$H NMR (CDCl$_3$, 298K) δ: 3.53 (td, 2H), 4.52 (s, 2H), 4.82 (s, 2H), 4.83 (s, 1H), 5.96 (tt, 1H), 7.37 (d, 1H), 7.55 (dd, 1H), 8.27 (d, 1H)

The invention claimed is:

1. A process for preparing a compound of formula (I)

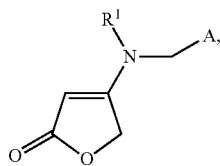

(I)

comprising reacting a compound of formula (II)

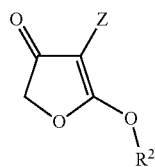

(II)

with an amine of formula (III)

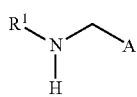

(III)

in the presence of a Brønsted acid, where
R$^1$ is hydrogen, alkyl, or haloalkyl;
R$^2$ is alkyl, haloalkyl, alkenyl, haloalkenyl, alkynyl, cycloalkyl, cycloalkylalkyl, halocycloalkyl, alkyloxyalkyl, halocycloalkylalkyl, aryl or arylalkyl;
Z is selected from the chemical moieties —(C=O)OR$^3$ and —(C=O)NR$^1$CH$_2$A, in which R$^3$ is selected from C$_{1-12}$-alkyl, C$_{3-8}$-cycloalkyl, C$_{2-12}$-alkenyl, C$_{2-12}$-alkynyl, C$_{6-8}$-aryl, C$_{7-19}$-arylalkyl or C$_{7-19}$-alkylaryl, each of which may be substituted by one or more radicals selected from —R', —OR', —SR', —NR'$_2$, —SiR'$_3$, —COOR', —(C=O)R', —CN and —CONR$_2$', where R' is hydrogen or C$_{1-12}$-alkyl;
A is pyrid-2-yl or pyrid-4-yl, or is pyrid-3-yl which is optionally 6-substituted by fluorine, chlorine, bromine, methyl, trifluoromethyl or trifluoromethoxy.

2. The process according to claim 1, wherein the Brønsted acid is selected from the group consisting of H$_3$PO$_4$, H$_2$SO$_4$, HCl, HBr, HF, KHSO$_4$, trifluoroacetic acid, acetic acid, methanesulphonic acid and p-toluenesulphonic acid.

3. The process according to claim 1, where
R$^1$ is hydrogen, C$_{1-12}$-alkyl, or C$_{1-12}$-haloalkyl;
R$^2$ is C$_{1-12}$-alkyl, C$_{1-12}$-haloalkyl, C$_{2-12}$-alkenyl, C$_{2-12}$-haloalkenyl, C$_{2-12}$-alkynyl, C$_{3-8}$-cycloalkyl, C$_{3-8}$-cycloalkylC$_{1-12}$-alkyl, C$_{3-8}$-halocycloalkyl, C$_{1-12}$-alkoxy, C$_{1-12}$-alkyloxyalkyl, C$_{3-8}$-halocycloalkylC$_{1-12}$-alkyl or C$_{6-14}$-ArylC$_{1-12}$-alkyl;
Z is selected from the chemical moieties —(C=O)OR$^3$ and —(C=O)NR$^1$CH$_2$A, in which R$^3$ is selected from C$_{1-12}$-alkyl, C$_{3-8}$-cycloalkyl, C$_{2-12}$-alkenyl, C$_{2-12}$-alkynyl, C$_{6-8}$-aryl, C$_{7-19}$-arylalkyl or C$_{7-19}$-alkylaryl, each of which may be substituted by one or more radicals selected from —R', —OR', —SR', —NR'$_2$, —SiR'$_3$, —COOR', —(C=O)R', —CN and —CONR$_2$', where R' is hydrogen or C$_{1-12}$-alkyl;
A is pyrid-2-yl or pyrid-4-yl, or is pyrid-3-yl which is optionally 6-substituted by fluorine, chlorine, bromine, methyl, trifluoromethyl or trifluoromethoxy.

4. The process according to claim 1, where
A is 6-fluoropyrid-3-yl, 6-chloropyrid-3-yl, 6-bromopyrid-3-yl, 5 fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl, 5-chloro-6-iodopyrid-3-yl or 5-difluoromethyl-6-chloropyrid-3-yl;
R$^1$ is methyl, ethyl, n-propyl, isopropyl, 2-fluoroethyl, or 2,2-difluoroethyl;
Z is a chemical moiety —(C=O)OR$^3$ in which R$^3$ is methyl, ethyl, n-propyl, isopropyl or butyl; and
R$^2$ is C$_1$-C$_{12}$-alkyl.

5. The process according to claim 1, where
A is 6-chloropyrid-3-yl, 6-bromopyrid-3-yl, 5-fluoro-6-chloropyrid-3-yl or 5-fluoro-6-bromopyrid-3-yl;
R$^1$ is methyl, ethyl, n-propyl, isopropyl, 2 fluoroethyl or 2,2-difluoroethyl;
Z is —CO$_2$CH$_2$CH$_3$ or —CO$_2$CH$_3$; and
R$^2$ is ethyl, isopropyl or butyl.

6. The process according to claim 1, wherein the reacting is performed in a solvent which is at least one selected from the group consisting of dioxane, butyronitrile, propionitrile, acetonitrile, DME, toluene, methyl-THF, dichlorobenzene, chlorobenzene, n-heptane, isobutanol, n-butanol, ethanol, methyl tert-butyl ether, and isopropyl ethyl ether.

7. The process according to claim 1, wherein the reacting is performed at a temperature from 20° C. to 150° C.

8. The process according to claim 1, wherein the molar ratio of the compound of the formula (II) to the compound of the formula (III) is 1 to 6.

9. The process according to claim 1, wherein compound (I) is 4-[[(6-chloropyridin-3-yl)methyl](2,2-difluoroethyl)amino]furan-2(5H)-one.

* * * * *